(12) United States Patent
Snell (10) Patent No.: US 6,766,198 B1
(45) Date of Patent: Jul. 20, 2004

(54) SYSTEM AND METHOD FOR PROVIDING PATIENT STATUS INFORMATION DURING INTERROGATION OF AN IMPLANTABLE CARDIAC STIMULATION DEVICE

(75) Inventor: Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 415 days.

(21) Appl. No.: 09/927,763

(22) Filed: Aug. 9, 2001

(51) Int. Cl.$^7$ ................................................ A61N 1/37
(52) U.S. Cl. .................................................... 607/30
(58) Field of Search ............................. 607/30–32, 59, 607/60; 120/903

(56) References Cited

U.S. PATENT DOCUMENTS

| | | | | |
|---|---|---|---|---|
| 5,690,690 A | * | 11/1997 | Nappholz et al. | 607/30 |
| 5,716,382 A | * | 2/1998 | Snell | 607/30 |
| 5,722,999 A | | 3/1998 | Snell | 607/32 |
| 5,724,985 A | | 3/1998 | Snell et al. | 128/697 |
| 5,725,559 A | * | 3/1998 | Alt et al. | 607/5 |
| 5,817,137 A | * | 10/1998 | Kaemmerer | 607/59 |
| 5,833,623 A | * | 11/1998 | Mann et al. | 600/523 |
| 6,168,563 B1 | | 1/2001 | Brown | 600/301 |
| 6,512,954 B2 | | 1/2003 | Fox et al. | 607/31 |
| 2003/0139785 A1 | * | 7/2003 | Riff et al. | 607/60 |

* cited by examiner

*Primary Examiner*—Kennedy Schaetzle
*Assistant Examiner*—Kristen Droesch (57) ABSTRACT

Upon interrogating a pacemaker, implantable cardioverter defibrillator or other implantable cardiac stimulation device, an external programmer accesses previously-stored physician comments maintained within the implanted device. The programmer disables any reprogramming of the implanted device until the physician comments have been displayed via the programmer for review by the physician or other medical professional seeking to reprogram the implanted device. In this manner, critical information pertaining to a previous programming session is presented to the physician before any additional reprogramming is permitted so as to ensure that the critical information is reviewed. In one example described herein, physician comments are designated as being either general or parameter-specific. General comments are displayed for review before any reprogramming is permitted. Parameter-specific comments are displayed for review only if the physician seeks to reprogram particular parameters associated therewith. Also described herein is a clearinghouse for storing large quantities of patient information and a method for accessing information stored in the clearinghouse. The clearinghouse permits large quantities of information that might otherwise not be appropriate for storage within the implanted device to be conveniently retrieved by an external programmer during a programming session for review by a physician. The clearinghouse may store, for example, the entire medical records of a patient or may store detailed information regarding the particular model of medical device implanted within the patient.

23 Claims, 6 Drawing Sheets

SYSTEM AND METHOD FOR PROVIDING PATIENT STATUS INFORMATION DURING INTERROGATION OF AN IMPLANTABLE CARDIAC STIMULATION DEVICE

CROSS-REFERENCE TO RELATED APPLICATIONS

This application is related to copending, commonly-assigned U.S. patent application Ser. No. 09/870,606, filed May 30, 2001, entitled SYSTEM AND METHOD FOR PROVIDING PATIENT STATUS INFORMATION DURING INTERROGATION OF AN IMPLANTABLE CARDIAC STIMULATION DEVICE.

FIELD OF THE INVENTION

The invention generally relates to external programmers for use with implantable cardiac stimulation devices and to programming methods for programming with implantable cardiac stimulation devices.

BACKGROUND OF THE INVENTION

Implantable cardiac stimulation devices, particularly pacemakers and implantable cardioverter-defibrillators (ICDs), are often configured to be used in conjunction with an programmer which allows a physician to program the operation of the implanted device to, for example, control the specific parameters by which the implanted device detects arrhythmia conditions and responds thereto. For instance, the programmer may allow the physician to specify the sensitivity with which the device senses electrical signals within the heart and to further specify the amount of electrical energy to be employed for pacing the heart in circumstances where expected heart signals are not sensed. Additionally, the programmer may be configured to receive and display a wide variety of diagnostic information detected by the implanted device, such as graphs of electrical heart signals sensed by the implanted device and responsive pacing signals. The programmer may operate to analyze the data received from the implanted device to assist the physician in rendering diagnoses as to possible arrhythmias and to assist the physician in programming the implantable cardiac stimulation device to provide appropriate therapy.

Current state of the art implantable cardiac stimulation devices have dozens or hundreds of control parameters that can be individually programmed using the external programmer. The programmable parameters permit the operation of the cardiac stimulation device to be tailored to the needs of the particular patient to provide optimal functionality while minimizing the risk of any unnecessary therapy. Unfortunately, it is often difficult to predict the effect of a selected set of parameter settings on a particular patient. Typically, a potentially viable set of parameters is chosen by the physician, the implantable cardiac stimulation device is programmed using the selected set of parameters, and then the patient is sent home. The various parameters selected by the physician as well as information pertaining to the patient are recorded within physician charts for the patient. Weeks or months later the patient must return to the physician for a follow-up appointment so that the physician may evaluate the affect of the selected parameters. Typically, the follow-up process consists of the physician making judgments based upon observing several characteristics of the patient and of the implanted cardiac stimulation device. If the implanted device is a pacemaker, the physician typically reviews internal electrocardiogram (IEGM) recordings and also reviews information pertaining to the operating status of the implanted device via telemetric interrogation of diagnostic data stored within the implanted device. The diagnostic data may, for example, specify the operation of the implanted device over the last few weeks or months. Specific types of diagnostic information that may be provided include information identifying the percentage of paced versus sensed beats, heart rate histograms, sensor rate histograms, etc. Additional diagnostic information specifies the battery voltage, lead impedances, etc. of the implanted device. The physician collates this information and makes adjustments to the programming of the pacemaker. Preferably, the aforementioned physician charts are updated for the patient to reflect the adjustments to the parameters and any additional diagnostic information on behalf of the patient, such as new or different symptoms experienced by the patient. Again, the patient is sent home for several more weeks or months until another follow-up visit. This cycle may be repeated numerous times before optimal device settings are determined by the physician. In many cases, the follow-up sessions are performed by different physicians. In some cases, the initial physician is simply unavailable during the follow-up session. In other cases, the patient consults another physician in a different geographical area for the follow-up session.

As can be appreciated, given the number of parameters that may need to be programmed, and the particular needs of the patient, many decisions may need to be made during each programming session and, in some cases, compromises may need to be made to what otherwise might be regarded as optimal programming settings. Communication of these decisions from the physician associated with one programming session to another therefore may be crucial in making an accurate assessment in a subsequent programming session. As noted, information of this type is written into the patient medical chart. Unfortunately, if the chart is not available or if it is not consulted by the physician in the follow-up session, then an inaccurate assessment of the needs of the patient may be made possibly resulting in improper programming of the implantable cardiac stimulation device. One solution that has been proposed is to store additional administrative information in the implantable cardiac stimulation device itself via the programmer. Thereafter, during a follow-up session, the physician may download the administrative information from the implantable cardiac stimulation device and review the administrative information before conducting any further programming of the implanted device. Unfortunately, even if administrative information is stored in the implantable cardiac stimulation device by a first physician, the physician of the follow-up session may be unaware of the information and therefore may not review the information prior to performing any re-programming operations. In other cases, the physician of the follow-up session may review the first portion of a potentially lengthy diagnostic assessment provided by a previous physician and conclude therefrom that the assessment does not contain information pertinent to the particular parameters being reprogrammed. In such cases, information pertaining to the programming of particular parameters may not be taken into account by the physician of the follow-up session resulting in non-optimal and possibly erroneous programming of the implanted device.

Accordingly, it would be highly desirable to provide an improved technique for incorporating administrative information into an implantable cardiac stimulation device which ensures that the physician of a follow-up session reviews the information before reprogramming the implanted device and it is to this end that aspects of the invention are primarily directed.

Moreover, the amount of administrative information to be maintained on behalf of the patient may be too large to efficiently store within the implanted device itself, such as complete patient histories, IEGM charts and the like. Accordingly, it also would be highly desirable to provide an improved technique for maintaining large amounts of information on behalf of a patient that can be expediently accessed by the physician before re-programming the implanted device and it is to this end that other aspects of the invention are directed.

SUMMARY OF THE INVENTION

In accordance with one aspect of the invention, an external programmer is provided for use in programming an implantable cardiac stimulation device implanted within a patient. The external programmer operates to detect the initiation of a programming session with the implantable cardiac stimulation device, retrieve administrative information previously stored within the implantable cardiac stimulation device, such as physician comments and diagnostic information, and display the information for review before permitting any programming of the implantable cardiac stimulation device.

Hence, a physician or other medical professional seeking to reprogram the implantable device is automatically provided with a display of previous physician comments or other administrative information before any reprogramming is permitted. By providing a control system which does not permit reprogramming of the implantable cardiac stimulation device until previously stored comments have been displayed for the physician, the risk that the physician may fail to review the previously stored physician comments is substantially eliminated thereby helping to ensure optimal reprogramming of the device.

In an exemplary embodiment, the implantable cardiac stimulation device is a pacemaker or an ICD. The external programmer includes an input device for receiving physician comments or other information which, subject to the control of the control device, are transmitted to the implantable cardiac stimulation device via the telemetry device for storage therein. Exemplary types of physician comments include patient diagnosis data, implantable cardiac stimulation device data, patient-device interaction data, physician contact data and family contact data. The input device also receives a priority code designated by the physician associated with selected portions of the physician comments. Thereafter, the control device controls the display device to display physician comments retrieved from the implantable device in order of priority based upon the priority codes to ensure that the most critical information is presented first.

Also in the exemplary embodiment, the control device stores a parameter code associated with selected physician comments to ensure the selected comments are stored only in connection with particular parameters to which the comments pertain. Upon initiation of a subsequent programming session, the selected comments are retrieved and displayed only if the physician seeks to reprogram the parameters associated with the comments. In this manner, the physician need not be burdened with reviewing comments which do not pertain to parameters that the physician is seeking to reprogram. On the other hand, if the physician needs to reprogram the particular parameters, the physician's attention is thereby directed to the comments specific to the parameters to be reprogrammed.

In accordance with another aspect of the invention, a clearinghouse is provided for storing information for a plurality of patients for use with an external programmer for programming an implantable cardiac stimulation device. The external programmers has a telemetry device for receiving administrative information transmitted from the implantable device of a patient. The administrative information received from the implantable cardiac stimulation device includes clearinghouse access information, such as a password, for use in accessing patient data for the respective patient stored within the clearinghouse. The external programmer forwards the password or other the clearinghouse access information to the clearinghouse, which responds by forwarding any information stored therein on behalf of the patient to the external programmer or to some other device specified by the external programmer such as a facsimile machine in proximity to the external programmer.

In this manner, large quantities of information that might otherwise not be appropriate for storage within the implanted device may be conveniently maintained in the clearinghouse for easy and automatic retrieval by an external programmer during a programming session. In an exemplary embodiment, the entire medical charts or records of a patient are scanned into a computer by a physician programming a device implanted with a patient for storage within the clearinghouse thus permitting any physician re-programming the implanted device during a subsequent programming session to easily access the entire patient's records and charts.

Other objects, features and advantages of the invention are described below. System and method embodiments of the invention are provided.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
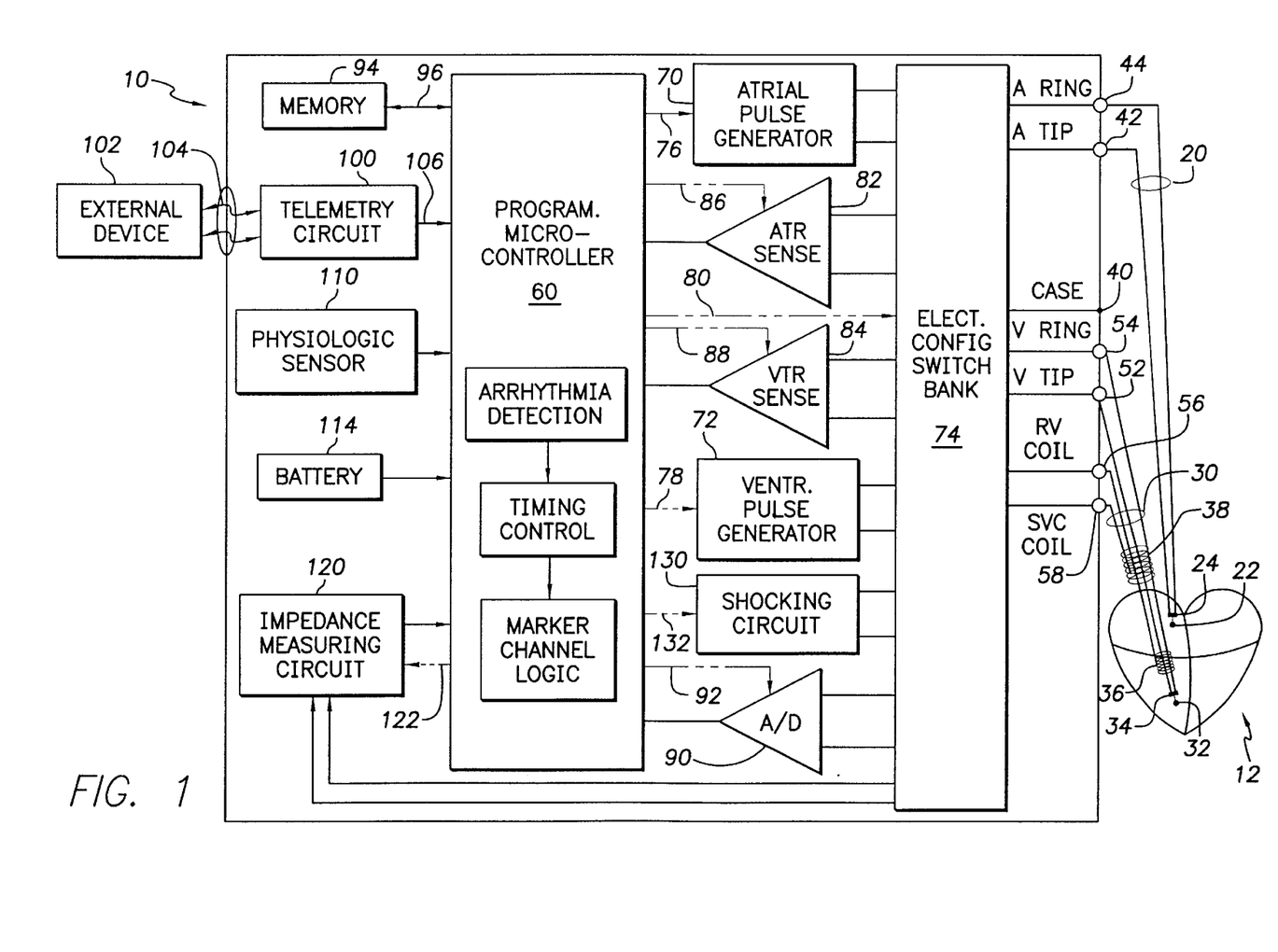
FIG. 1 is a functional block diagram of a dual-chamber implantable stimulation device illustrating the basic elements of a stimulation device which can provide cardioversion, defibrillation and pacing stimulation and can predict and prevent vasovagal syncope in accordance with an exemplary embodiment of the invention.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, band pass filtering, and a threshold detection circuit, known in the art, to selectively sense the cardiac signal of interest. The automatic gain control enables the implanted device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers. For arrhythmia detection, the present device utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer, to be described in greater detail below. The telemetry circuit 100 is activated by the microcontroller by a control signal 106. The telemetry circuit 100 advantageously allows intracardiac electrograms and status information relating to the operation of the implanted device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the stimulation device 10, which employs shocking therapy, the battery must be capable of operating at low current drains for long periods of time and then be capable of providing high-current pulses (for capacitor charging) when the patient requires a shock pulse. The battery 114 must also have a predictable discharge characteristic so that elective replacement time can be detected. Accordingly, the implanted device employs lithium/silver vanadium oxide batteries, as is true for most (if not all) such devices to date.

It is the primary function of the invention to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11–40 Joules), as controlled by the microcontroller 60. Such shocking pulses are applied to the patient's heart 12 through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
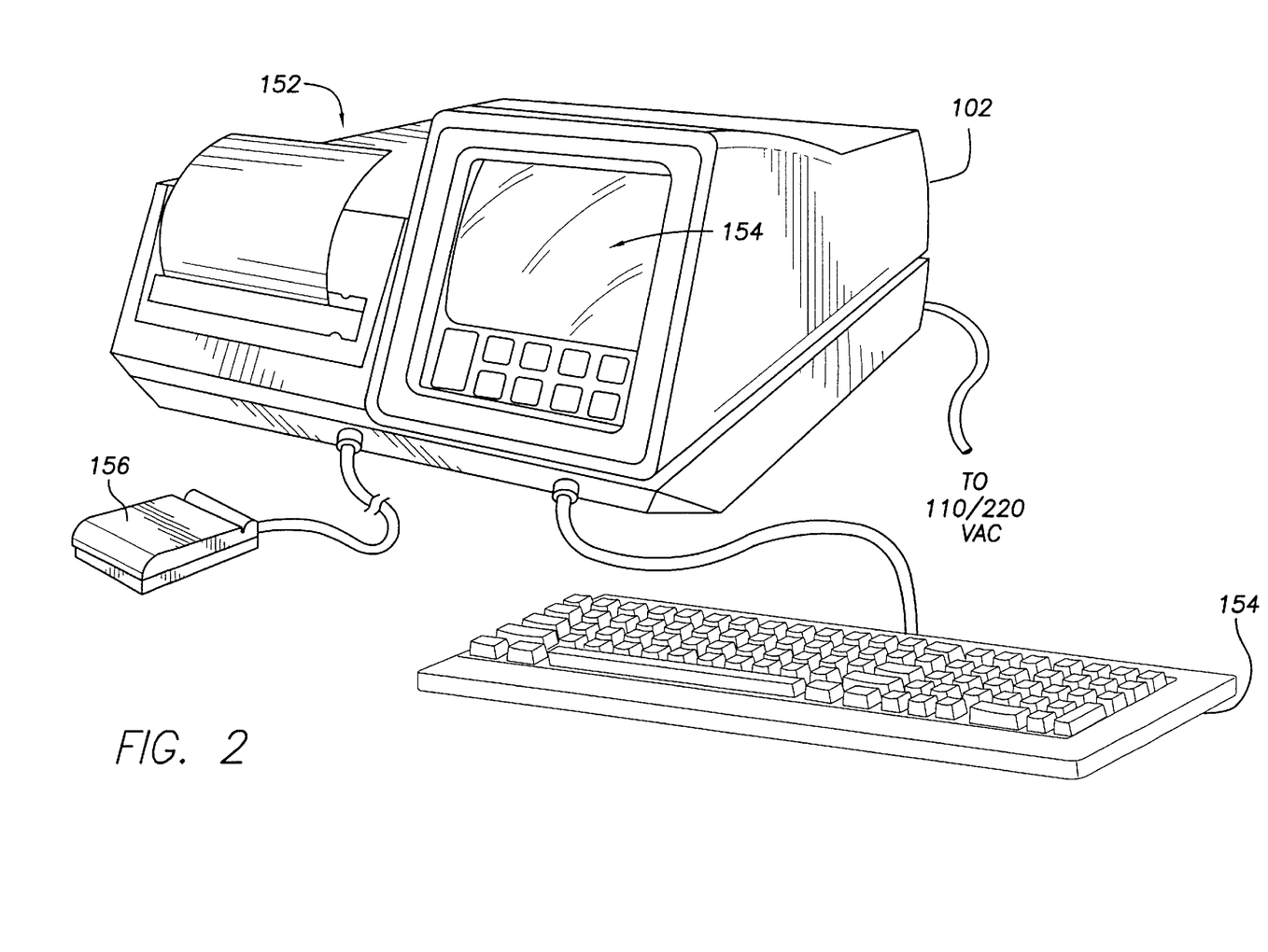
FIG. 2 is illustrates an external programmer for use in programming the implantable device of FIG. 1.

FIG. 2 illustrates an external programmer 102 configured for programming stimulation device 10 (FIG. 1) and for displaying information received from the implanted device such as administrative information. Table I provides a list of a few exemplary programming parameters employed by the external programmer to program the operation of the pacemaker.

TABLE I

| PROGRAMMING PARAMETER | PROGRAMMED FUNCTION |
| --- | --- |
| Mode | Pacemaker Mode Programmed |
| Base Rate | Heart Base Rate Programmed |
| Rest Rate | Heart Rest Rate Programmed |
| Maximum Tracking Rate | Maximum Pacemaker Tracking Rate Programmed |
| Maximum Sensor Rate | Maximum Pacemaker Sensor Rate Programmed |
| Rate Responsive AV/PV Delay | Rate Responsive AV/PV Delay Programmed |

Programmer 102 includes a printer 152 for printing a graphical representation of the information received from the pacemaker and a display screen 154 for providing a graphical representation of the information such as, for example, ECGs. The programming of the pacemaker and the generation of graphic displays of information received from the pacemaker is subject to the control of a physician or other user operating the external programmer. To this end, external programmer 102 presents various menus on display screen 154 for use in controlling operation of the programmer to program pacemaker 10 (FIG. 1) using any of the parameters listed above in TABLE I. Various menus are also presented on display screen 154 for use in controlling operation of the programmer to generate displays on display screen 154 of parameters used to the pacemaker. Programmer 102 receives menu selections from the physician through a keyboard 154. Actual programming of the pacemaker is achieved using a telemetry head 156 which, in use, is placed is proximity to the pacemaker. The functions of the external programmer are controlled by software operating within a microprocessor or microcontroller, not separately shown. Among other functions the microprocessor operates as a control device for detecting the initiation of a programming session with device 10, for controlling telemetry head 156 to retrieve physician comments previously stored within the device 10, and for displaying the physician comments before permitting any reprogramming of device 10.

With reference to the remaining figures, various exemplary programming methods employed by the programmer of FIG. 2 in connection with the implanted device of FIG. 1 will now be described with reference to flow charts which provide an overview of the operation of various novel features of the invention. In the flow charts, various algorithmic steps are summarized in individual "blocks". Some of the steps are performed by the external programmer and others by the implanted device. The blocks describe specific actions or decisions made or carried out as the overall algorithm proceeds. Where microcontrollers (or equivalent) are employed, the flow charts presented herein provide the basis for a "control program" that may be used by such a microcontroller (or equivalent) to effectuate the desired control of the stimulation device or of the external programmer. Those skilled in the art may readily write such a control program based on the flow charts and other descriptions presented herein.

Figure 3:
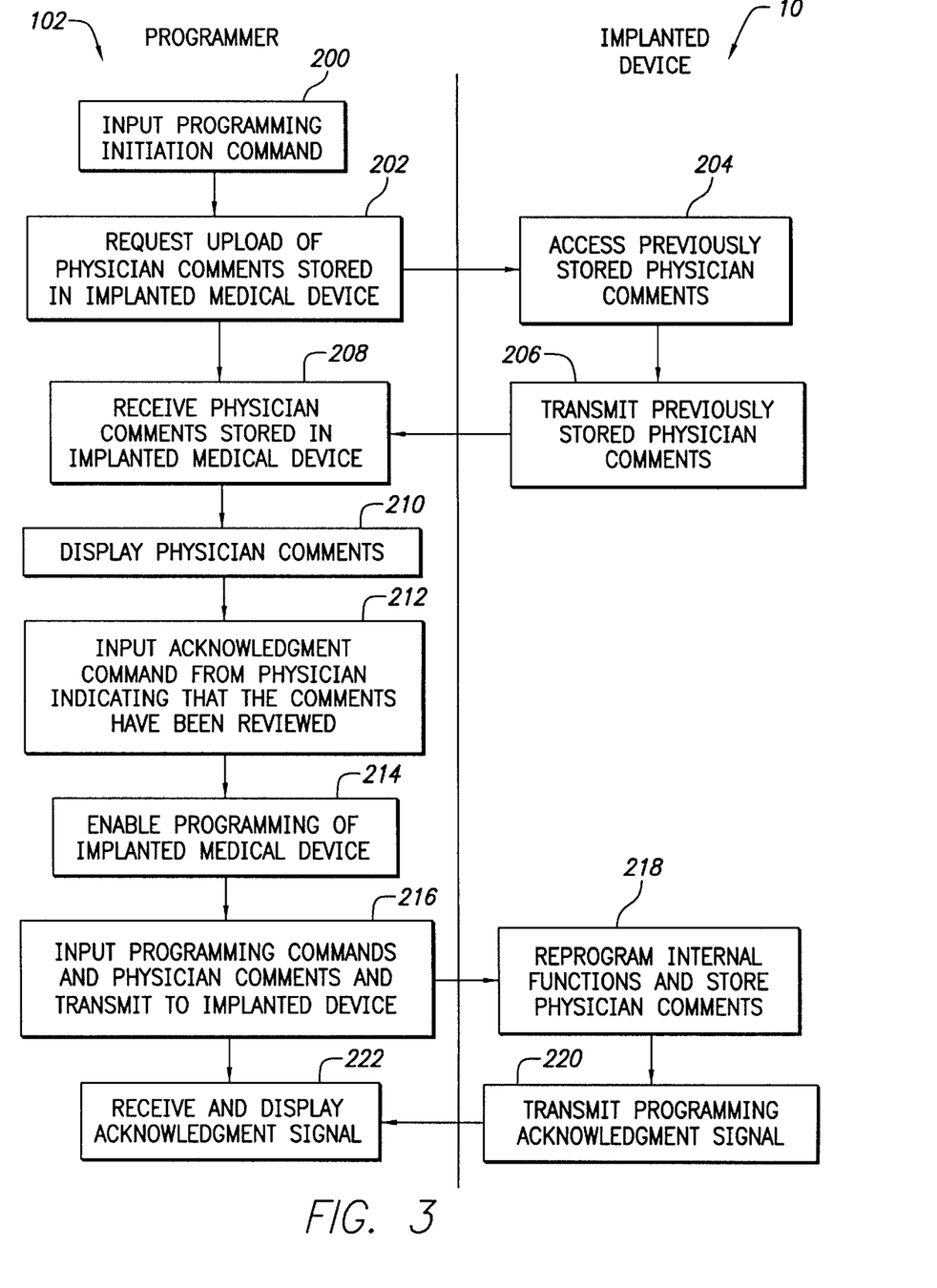
FIG. 3 is a flow chart illustrating a first exemplary programming method performed by the external programmer of FIG. 2 for programming the implantable device of FIG. 1.

FIG. 3 illustrates steps performed by the external programmer of FIG. 2 in tandem with steps performed by the implanted device of FIG. 1 while the programmer operates to program the implanted device under the control of a physician or other medical professional. Initially, at step 200, the external programmer inputs a programming initiation command from the physician. At step 202, the programmer then transmits signals to the implanted device for controlling the implanted device to transfer or upload any physician comments or other types of administrative information previously stored in the implanted device, perhaps as the result of a previous programming session involving a different physician at another hospital or clinic. In response, at step 204, the implanted device accesses its internal memory to determine if any comments are stored therein and, if so, transmits the comments to the external programmer at step 206. The comments, if transmitted, are received by the external programmer at step 208 and stored therein. In the alternative, rather than having the programmer query the implanted device for physician comments only upon initiation of a programming session, the programmer may automatically upload any physician comments upon initiation of any telemetry session between the programmer and the implanted device, as may be automatically initiated by placing the telemetry unit of the programmer over the implanted device of the patient.

Any physician comments received from the implanted device are displayed to the physician at step 210 for review by the physician. No programming of the implanted device is permitted until the physician has input an acknowledgement command at step 212 indicating that the comments have been reviewed. Depending upon the implementation, the acknowledgement command is an ENTER command or similar input keystroke. To prevent previously buffered keystrokes or other commands to be inadvertently accepted as an acknowledgement that the comments have been reviewed, the programmer ignores any keystrokes entered before the physician comments have been displayed. If more than one page of physician comments are provided, the programmer does not accept the acknowledgement command until all pages of comments have been displayed on the screen, as determined by detecting appropriate page down commands. Also, to help ensure that the comments are fully reviewed by the physician, the programmer may refuse entry of any acknowledgement command until some period of time has elapsed since the initial display of the comments, such as 15 seconds. The amount of time may be based upon the total amount of text presented in the comments, with a fairly short delay time associated with brief comments and a longer delay time associated with several pages of comments.

Once a valid acknowledgement command has been input, the programmer enables programming of the implanted device beginning at step 214. Prior to enablement, the programmer does not accept any programming commands or, if commands are accepted, does not forward the commands to the implanted device. As noted above, by disabling programming until physician comments have been reviewed, there is a greater likelihood that the physician will carefully review the comments and take the comments into account in adjusting any programming parameters. If programming could be performed without the programmer first displaying the comments, it is possible that the physician may not bother reviewing the comments and may not even be aware that there are comments that need to be reviewed.

Beginning at step 216, the physician enters various programming commands, such as any of the programming commands of Table I. Additionally, at step 216, the physician is invited to enter any comments that he or she may want to be displayed during a subsequent programming session. To this end, the programmer displays a text screen for entering any physician comments so as to facilitate easy entry of the comments. Also within step 216, the input programming commands and any physician comments are transmitted to the implanted device via the telemetry unit of the programmer. At step 218, the programming commands and comments are received by the implanted device and stored therein. Additionally, the implanted device reprograms its internal functions based upon the received programming commands so as to, for example, change the mode of operation, the base programming rate, or the sensitivity.

At step 220 one or more acknowledgement signals are transmitted to the external programmer acknowledging successful reprogramming of the implanted device and successful storage of the physician commands. Depending upon the implementation, different acknowledgement signals may be provided for separately acknowledging successful reprogramming of parameters as opposed to successful storage of physician comments. Additionally, separate acknowledgement signals may be transmitted for separately acknowledging successful reprogramming of particular functions. In this manner, if only certain programming commands are not properly received, the programmer need not re-transmit all programming commands and all comments but may instead re-transmit only those commands or comments which were not successfully received by the implanted device. In any case, the acknowledgement signals are received and displayed to the physician at step 222. The physician may perform additional programming operations or may enter additional physician comments by returning to step 216.

Thus FIG. 3 illustrates a method for disabling programming of an implanted device until previously stored comments have been displayed via the external programmer for review by the physician or other person operating the programmer. Depending upon the implementation, both text and non-text-based comments may be accommodated including, for example, graphical displays of IEGM patterns that the physician may feel should be reviewed before any reprogramming of the device. Any of a wide variety of information may be provided for storage within the implanted device, depending upon a particular programming of the overall system. Exemplary types of information include comments pertaining to the patient diagnosis, the implanted cardiac stimulation device, patient-device interactions, physician contact information and family contact information. Preferably, only particularly critical or unusual types of information are stored within the implanted device and routine information is simply recorded by the physician within conventional medical charts for the patient. In this manner, memory within the implanted device is not consumed by comments that are not particular critical. Generally, the physician employs discretion over the types of information to be stored, with the understanding that further programming of the implanted device will be disabled until those comments are reviewed. Types of comments that are particularly appropriate include comments pertaining to any programming parameters which would not otherwise appear to be optimal parameters. As another example, comments may pertain to medications to be taken by the patient, particularly if the patient has a history of failing to take required medications thereby yielding physical symptoms that might otherwise be misinterpreted as non-optimal programming of the implanted device. Whether or not the physician decides to store comments may depend upon whether the patient routinely visits a single physician or multiple physicians. If the patient routinely visits a single physician, that physician may find no need to store comments within the implanted device. However, if the patient routinely visits different physicians at different locations, each physician may prefer to include comments for review by the other physicians before reprogramming by the other physicians is permitted.

Figure 4:
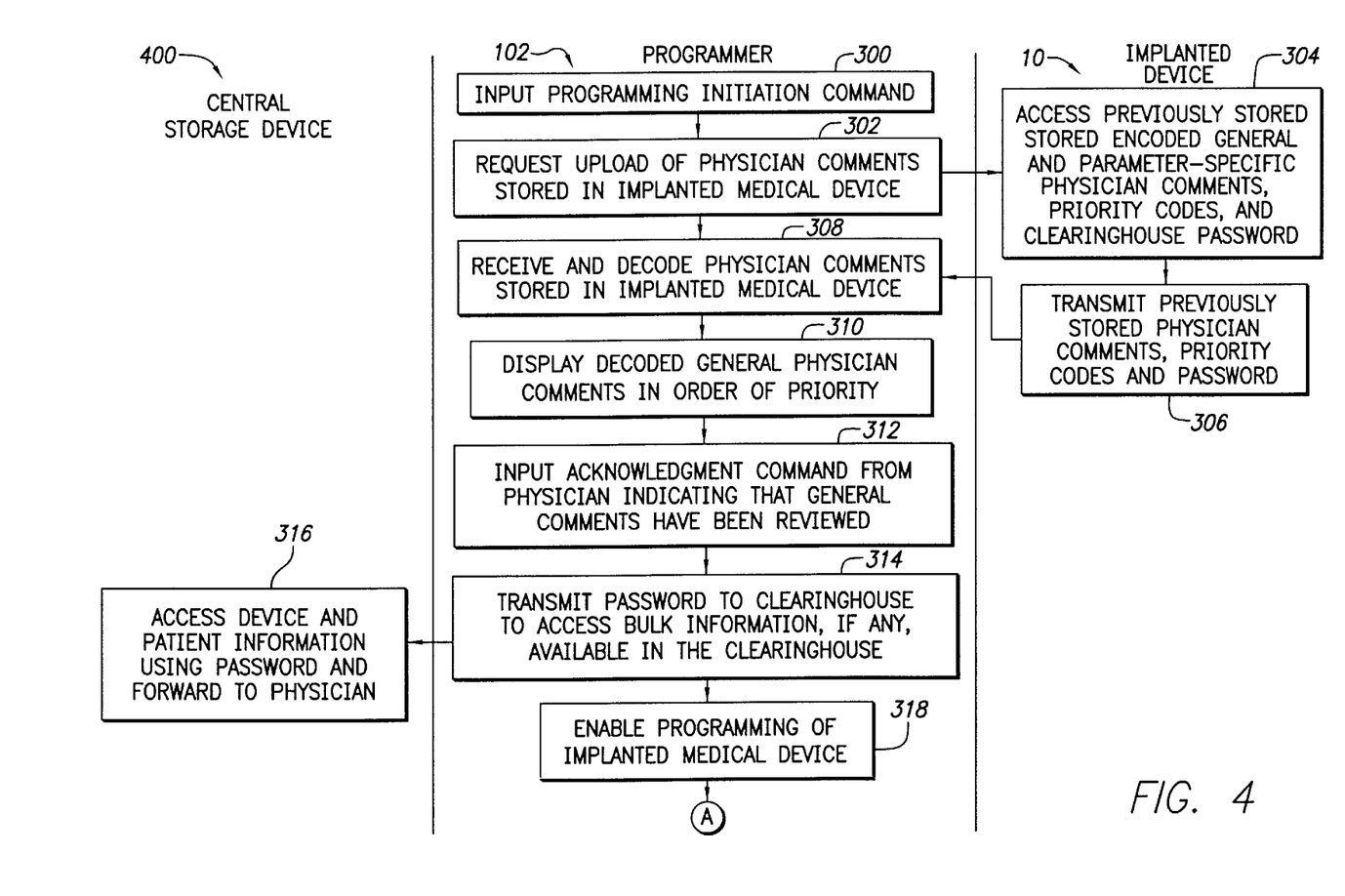
FIG. 4 is a first portion of a flow chart illustrating of a second exemplary programming method performed by the external programmer of FIG. 2 for programming the implantable device of FIG. 1.
Figure 5:
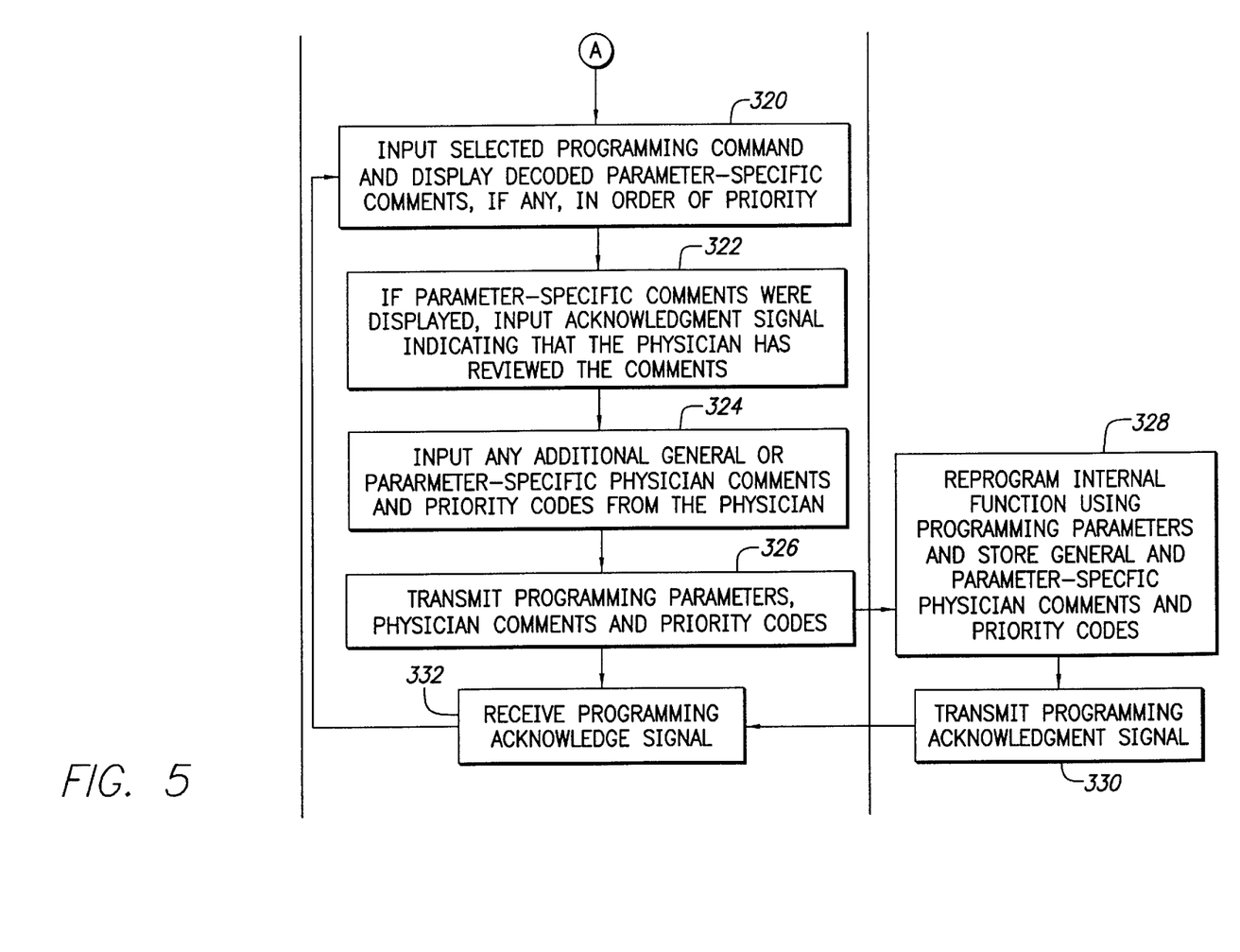
FIG. 5 is a second portion of the flow chart of FIG. 4.

Thus, what has been described with reference to FIG. 3, is one example of a method for incorporating physician comments within an implanted device and for disabling programming of the implanted device until the comments have been displayed for review by a physician. With reference to FIGS. 4 and 5, an alternative programming method is provided which additionally provides: prioritization of physician comments to ensure the most critical comments are displayed first; separate storage of general comments and parameter-specific comments to permit display of certain comments only if particular parameters are to be reprogrammed; and storage of a password or other information for accessing a centralized clearinghouse of information to permit easy access to bulk information which may not be appropriate for storage within the implanted device itself. Within FIGS. 4 and 5, operations of the central clearinghouse, the programmer, and the implanted device are shown in tandem.

Initially, within FIG. 4, at step 300, the programmer inputs a programming initiation command and, at step 302, transmits signals to the implanted device requesting transference of any physician comments stored within the implanted device. At step 304, the implanted device accesses any previously stored physician comments and transmits the comments to the external programmer. Additionally, the implanted device accesses and transmits any priority codes associated with the comments and any clearinghouse access information, such as passwords or phone numbers for accessing clearinghouse information. The various types of information are transmitted at step 306 to the programmer for receipt therein at step 308. To minimize the amount of memory consumed within the implanted device, all or a portion of the physician comments may be compressed. If so, then, at step 308 the comments are decompressed for complete display. Additionally, or in the alternative, certain predetermined codes may be associated with types of information to be commonly stored within physician comments and, if so, the programmer at step 308 replaces the codes with more readable expanded text in accordance with preprogramming.

At step 310 any general physician comments, decoded or decompressed as needed, are displayed by the programmer in order of priority. By "general" physician comments, it is meant that the comments were designated by the physician storing the comments as being generally applicable to any type of reprogramming of the implanted device. Hence, general comments are displayed before any programming is permitted. "Parameter-specific" physician comments are displayed only in the event that the physician of the current programming session attempts to reprogram the particular parameters associated therewith. Also within step 310, the comments are displayed in the order of priority so as to ensure that the most pertinent or critical comments are displayed first with less important comments displayed subsequently. Depending upon the programming of the system, comments of differing priority are displayed distinctly by the programmer using display-style priority codes. For example, comments of highest priority are displayed in red, underlined, and/or blinking, whereas comments of lower priority are simply presented in plain text. Additionally, for comments of high priority, audible signals may be generated by the programmer to draw particular attention to the comment.

At step 312, the programmer inputs an acknowledgement command from the physician indicating that the general comments have been reviewed. At step 314, if a clearinghouse password or other clearinghouse access information was received from the implanted device, the programmer automatically accesses the central clearinghouse to receive bulk information pertaining to the patient or to the implanted device, at step 316. For example, if the programmer is connected to the Internet, the clearinghouse information may specify an Internet site for accessing information pertinent to the implanted device or the patient for display on the programmer. In other cases, the clearinghouse information may provide a telephone number and password for accessing a central automated clearinghouse which automatically transmits information via facsimile back to the external programmer or to a facsimile machine connected thereto. In this manner, large quantities of information that might otherwise not be appropriate for storage within the implanted device may be easily and automatically accessed. As one specific example, the entire medical charts or records of the patient may be scanned in to a computer by a predecessor physician for storage within the clearinghouse to thereby permit a subsequent physician to easily access the patient records and charts. In still other cases, the clearinghouse information may specify the telephone number for the primary physician for the patient to thereby alert the primary physician that the implanted device of his or her patient may be subject to reprogramming and to thereby place the primary physician in contact with the physician handling the reprogramming via telephone, if the primary physician is available. As can be appreciated, a wide range of other types of information may be accessible via any centralized clearinghouse of information and no attempt is made herein to list all possible types of information or access codes that may be employed. At step 318, the programmer enables programming of the implanted device.

Turning now to FIG. 5, once the physician has selected a first programming command for reprogramming one or more selected parameters of the implanted device, the programmer accesses and displays any parameter-specific comments pertaining to any of the parameters to be reprogrammed by the selected command at step 320. As with the general comments discussed above, the specific display mode of the parameter-specific comments may depend upon the priority. Also, at step 320, if any of the parameter-specific comments were previously compressed or encoded, the programmer decompresses or decodes the comments as necessary for display. If parameter-specific comments are displayed at step 320, then step 322 is performed to receive an acknowledgement signal from the physician indicating that the comments have been reviewed. At step 324 the physician has the opportunity to add additional comments for storage in the implanted device, along with appropriate prioritization codes and to add or modify clearinghouse access information. The comments entered at step 324 may be designated by the physician as general comments or parameter-specific comments.

At step 326, the programming parameters and any physician comments, prioritization codes or other information are transmitted to the implanted device and are received and processed therein at step 328. Appropriate acknowledgement signals are transmitted from the implanted device at step 330 for processing and display by the programmer at step 332. Thereafter, the programmer returns to step 320 to permit the physician to select other programming commands. Programmer steps 320–332 are repeated as needed until the physician has programmed any and all selected parameters of the implanted device.

Thus, FIGS. 4 and 5 illustrate a method providing, among other features, for the storage of parameter-specific comments which are displayed during a subsequent programming session only if parameters associated with the comments are to be affected by any particular programming commands entered by the physician. In this manner, a subsequent physician need not be bothered by the display of comments not pertinent to the particular parameters being reprogrammed. The method includes access to a central clearinghouse of information.

Figure 6:
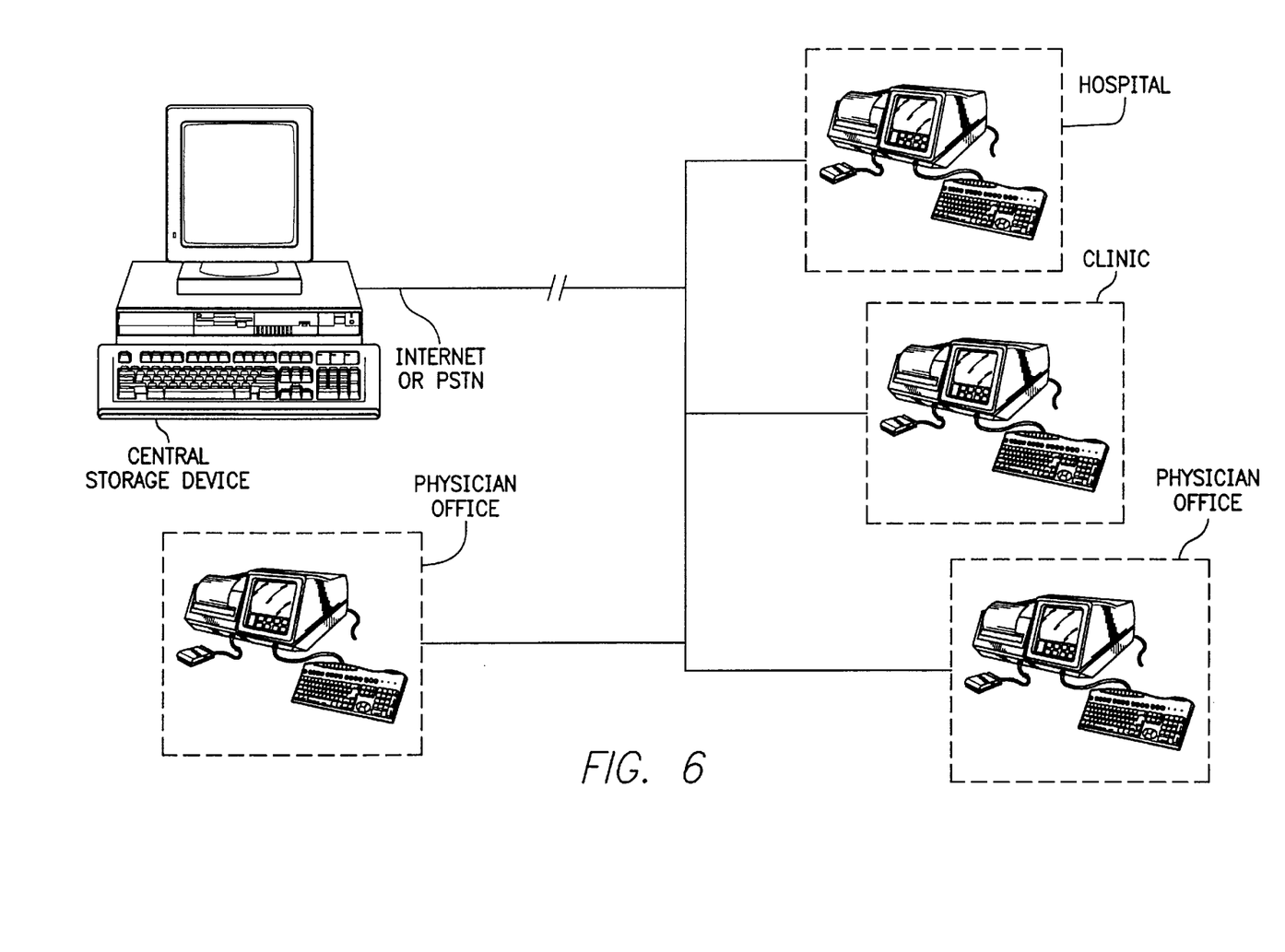
FIG. 6 is a block diagram illustrating a central clearinghouse of patient information accessed by the method of FIGS. 4 and 5.

The central clearinghouse of information is illustrated in FIG. 6 and defines a central data repository or storage device that preferably includes a server or other interface device that allows for interaction with remote devices over a communication network. Central clearinghouse 400 is provided for use with a distributed network of external programmers 402 installed within hospitals, clinics or physician offices. In the specific implementation of FIG. 6, the external programmers communicate with the central clearinghouse via the public switched telephone network (PSTN) or other land line communication link, such as T1 line, ISDN line, or via the Internet. Alternatively, individual external programmers may be provided with wireless communication devices to permit the external programmers to communicate with the clearinghouse via satellite-based wireless communication systems, cellular telephone systems, or the like.

The central clearinghouse stores and maintains bulk patient information which may not be appropriate or efficient for storage within individual implanted devices or within the programmers themselves, such as complete patient histories, patient charts, bulk IEGM data etc. The clearinghouse also stores other bulk information which may not be efficient for storage within individual implanted devices or programmers, such as detailed engineering or operational data pertaining to the particular model of the implanted device. During programming of an implanted device using one of the external programmers, the implanted device being programmed accesses a password or other clearinghouse access information stored therein and transmits the password to the external programmer. The external programmer can then access the clearinghouse using the password or other access information to retrieve any bulk information stored therein, including any information pertinent to the particular patient or to the particular model of implanted device. In addition to a password, the clearinghouse access information also includes the phone number for connecting the external programmer to the clearinghouse if telephonic connection via a PSTN is required. If connection via the Internet is permitted, the clearinghouse access information also includes the web site address for accessing the clearinghouse.

The clearinghouse then transmits the bulk information to the external programmer via the clearinghouse/programmer interconnection line or transmits the information via facsimile to a facsimile machine in proximity to the programmer as specified by a telephone number provided by the programmer or in other suitable manner. During a programming session, the external programmer can also update the data stored in the clearinghouse by transmitting additional patient information to the clearinghouse, such as recently downloaded IEGM data, so that the updated date can be retrieved from the clearinghouse during a subsequent programming session.

What have been described are various techniques for incorporating physician comments within an implanted device and for maintaining a clearinghouse of information. Although described primarily with reference to an example wherein the implanted cardiac stimulation device is a pacemaker or ICD, principles of the invention are applicable to other implanted devices as well. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method for programming an implantable cardiac stimulation device for implant within a patient using an external programmer, the method comprising the steps of:

detecting initiation of a programming session with the implantable device and automatically retrieving administrative information from the implantable cardiac stimulation device;

displaying the administrative information until an acknowledgement that the displayed administrative information had been reviewed is input by an operator of the external programmer;

inputting programming commands to be transmitted to the implantable cardiac stimulation device; and transmitting the programming commands to the implantable cardiac stimulation device;

with the steps of inputting and transmitting programming commands to the implantable device being automatically suspended until the acknowledgement has been input.

2. The method of claim 1 wherein the administrative information retrieved from the implantable cardiac stimulation device includes one or more of patient diagnosis data, implantable cardiac stimulation device data, patient-device interaction data, physician contact data, and family contact data.

3. The method of claim 1 wherein the external programmer is used in conjunction with a clearinghouse for storing information for a plurality of patients and wherein the administrative information retrieved from the implantable cardiac stimulation device includes clearinghouse access information for use in accessing information stored within the clearinghouse and wherein the method further includes the step of retrieving the information using the clearinghouse access information.

4. The method of claim 3 wherein the clearinghouse access information includes a password for accessing information within the clearinghouse.

5. The method of claim 1 wherein the administrative information retrieved from the implantable cardiac stimulation device includes display-order priority codes associated with selected portions of the diagnostic information and the administrative information is displayed in order of priority based on the display-order priority codes.

6. The method of claim 1 wherein the administrative information retrieved from the implantable cardiac stimulation device includes display-style priority codes associated with selected portions of the administrative information and the administrative information is displayed distinctly based on the display-style priority codes.

7. The method of claim 1 wherein portions of the administrative information retrieved from the implantable cardiac stimulation device are designated as either general administrative information or parameter-specific administrative information and wherein general administrative information is displayed before permitting transmission of any programming commands to the implantable device and parameter-specific administrative information is displayed only if parameters associated therewith are to be transmitted to the implantable device.

8. An external programmer for programming an implantable cardiac stimulation device for implant within a patient, the external programmer comprising:
   an input device operative to input programming commands;
   a telemetry device operative to transmit programming commands to the implantable cardiac stimulation device and to receive administrative information transmitted from the implantable cardiac stimulation device;
   a display device operative to display administrative information; and
   a control device operative to control the telemetry device to receive administrative information stored within the implantable cardiac stimulation device and to disable inputting programming commands and transmitting programming commands to the implantable cardiac stimulation device until the administration information has been displayed for review by an operator.

9. The external programmer of claim 8 wherein the implantable cardiac stimulation device is a pacemaker or implantable cardioverter defibrillator.

10. The external programmer of claim 8 wherein the input device is also operative to input administrative information for storage in the implantable device and wherein the control device is also operative to control the telemetry device to transmit the input administrative information to the implantable cardiac stimulation device for storage therein.

11. The external programmer of claim 8 wherein the telemetry device is operative to receive, as administrative information, one or more of patient diagnosis data, implantable cardiac stimulation device data, patient-device interaction data, physician contact data, and family contact data.

12. The external programmer of claim 8 used in conjunction with a clearinghouse for storing information for a plurality of patients and wherein the telemetry device is operative to receive, as administrative information, clearinghouse access information for use in accessing information stored within the clearinghouse.

13. The external programmer of claim 12 wherein the telemetry device is operative to receive, as administrative information, a password for accessing information within the clearinghouse.

14. An external programmer for programming an implantable cardiac stimulation device for implant within a patient, the external programmer comprising:
   means for receiving administrative information transmitted from the implantable cardiac stimulation device;
   means for displaying administrative information;
   means for transmitting programming commands to the implantable cardiac stimulation device; and
   a control device operative to control the means for receiving to receive administration information stored within the implantable cardiac stimulation device and to disable the means for transmitting programming commands to the implantable cardiac stimulation device until the administration information has been displayed for review by an operator.

15. The external programmer of claim 14 wherein the means for receiving administrative information receives one or more of patient diagnosis data, implantable cardiac stimulation device data, patient-device interaction data, physician contact data, and family contact data.

16. The external programmer of claim 14 used in conjunction with a clearinghouse for storing information for a plurality of patients and wherein the means for receiving administrative information receives clearinghouse access information for use in accessing information stored within the clearinghouse.

17. The external programmer of claim 16 wherein the means for receiving administrative information receives a password for accessing information within the clearinghouse.

18. An external programmer for programming an implantable cardiac stimulation device for implant within a patient, the external programmer comprising:
   an input device operative to input programming commands;
   a telemetry device operative to transmit programming commands to the implantable cardiac stimulation device and to receive administrative information transmitted from the implantable cardiac stimulation device;
   a display device operative to display administrative information; and
   a control device operative to control the telemetry device to receive administrative information stored within the implantable cardiac stimulation device and to control the display device to display the administrative information before permitting transmission of programming commands to the implantable device using the telemetry device;
   wherein the telemetry device is operative to receive, as administrative information, display-order priority codes associated with selected portions of the administrative information and wherein the control device is operative to control the display device to display the administrative information in order of priority based on the display-order priority codes.

19. An external programmer for programming an implantable cardiac stimulation device for implant within a patient, the external programmer comprising:
   an input device operative to input programming commands;
   a telemetry device operative to transmit programming commands to the implantable cardiac stimulation device and to receive administrative information transmitted from the implantable cardiac stimulation device;
   a display device operative to display administrative information; and
   a control device operative to control the telemetry device to receive administrative information stored within the implantable cardiac stimulation device and to control the display device to display the administrative information before permitting transmission of programming commands to the implantable device using the telemetry device;

wherein the telemetry device is operative to receive, as administrative information, display-style priority codes associated with selected portions of the administrative information and wherein the control device is operative to control the display device to provide distinct displays of the administrative information based on the display-style priority codes.

20. An external programmer for Programming an implantable cardiac stimulation device for implant within a patient, the external programmer comprising:

an input device operative to input programming commands;

a telemetry device operative to transmit programming commands to the implantable cardiac stimulation device and to receive administrative information transmitted from the implantable cardiac stimulation device;

a display device operative to display administrative information: and a control device operative to control the telemetry device to receive administrative information stored within the implantable cardiac stimulation device and to control the display device to display the administrative information before permitting transmission of programming commands to the implantable device using the telemetry device;

wherein the telemetry device is operative to receive administrative information designated as either general diagnostic information or parameter-specific diagnostic information and wherein the control device is operative to control the display device to display general diagnostic information before permitting transmission of any programming commands to the implantable device and to control the display device to display parameter-specific diagnostic information only if parameters associated therewith are to be transmitted to the implantable device.

21. An external programmer for programming an implantable cardiac stimulation device for implant within a patient, the external programmer comprising:

means for receiving administrative information transmitted from the implantable cardiac stimulation device;

means for displaying administrative information;

means for transmitting programming commands to the implantable cardiac stimulation device; and means for controlling the means for receiving to receive administrative information stored within the implantable cardiac stimulation device and for controlling the means for displaying to display the administrative information before controlling the means for transmitting to transmit any programming commands to the implantable device;

wherein the means for receiving administrative information receives display-order priority codes associated with selected portions of the administrative information and wherein the means for controlling controls the means for displaying to display the administrative information in order of priority based on the display-order priority codes.

22. An external programmer for programming an implantable cardiac stimulation device for implant within a patient, the external programmer comprising:

means for receiving administrative information transmitted from the implantable cardiac stimulation device;

means for displaying administrative information;

means for transmitting programming commands to the implantable cardiac stimulation device; and means for controlling the means for receiving to receive administrative information stored within the implantable cardiac stimulation device and for controlling the means for displaying to display the administrative information before controlling the means for transmitting to transmit any programming commands to the implantable device;

wherein the means for receiving administrative information receives display-style priority codes associated with selected portions of the administrative information and wherein the means for controlling controls the means for displaying to provide distinct displays of the administrative information based on the display-style priority codes.

23. An external programmer for programming an implantable cardiac stimulation device for implant within a patient, the external programmer comprising:

means for receiving administrative information transmitted from the implantable cardiac stimulation device;

means for displaying administrative information;

means for transmitting programming commands to the implantable cardiac stimulation device; and means for controlling the means for receiving to receive administrative information stored within the implantable cardiac stimulation device and for controlling the means for displaying to display the administrative information before controlling the means for transmitting to transmit any programming commands to the implantable device;

wherein the means for receiving administrative information receives administrative information designated as either general diagnostic information or parameter-specific diagnostic information and wherein the means for controlling controls the means for displaying to display general diagnostic information before permitting transmission of any programming commands to the implantable device and to control the means for displaying to display parameter-specific diagnostic information only if parameters associated therewith are to be transmitted to the implantable device.

* * * * *